US008322674B2

(12) United States Patent
Metelski

(10) Patent No.: US 8,322,674 B2
(45) Date of Patent: Dec. 4, 2012

(54) SUSPENSION SYSTEM FOR A CEILING MOUNT OF A SURGICAL MICROSCOPE

(75) Inventor: Andrzej Metelski, Romanshorn (CH)

(73) Assignee: Leica Instruments (Singapore) Pte, Ltd., Singapore (SG)

( * ) Notice: Subject to any disclaimer, the term of this patent is extended or adjusted under 35 U.S.C. 154(b) by 759 days.

(21) Appl. No.: 12/390,116

(22) Filed: Feb. 20, 2009

(65) Prior Publication Data

US 2009/0212188 A1 Aug. 27, 2009

(30) Foreign Application Priority Data

Feb. 27, 2008 (DE) .................. 10 2008 011 311

(51) Int. Cl.
*A47H 1/10* (2006.01)
(52) U.S. Cl. ......... 248/317; 248/343; 378/193; 378/195
(58) Field of Classification Search .................. 248/317, 248/335, 330.1, 333, 278.1, 610, 323, 309.1, 248/343, 282.1, 289.11; 359/368, 369; 378/193, 378/195, 197
See application file for complete search history.

(56) References Cited

U.S. PATENT DOCUMENTS

| | | | | |
|---|---|---|---|---|
| 3,175,085 A | * | 3/1965 | Avery | 378/197 |
| 4,747,119 A | | 5/1988 | Heinz et al. | |
| 5,240,218 A | * | 8/1993 | Dye | 248/330.1 |
| 6,095,468 A | * | 8/2000 | Chirico et al. | 248/282.1 |
| 6,364,268 B1 | * | 4/2002 | Metelski | 248/317 |
| 7,481,410 B2 | * | 1/2009 | Umberg | 248/551 |
| 2006/0250685 A1 | * | 11/2006 | Metelski | 359/368 |
| 2007/0140435 A1 | * | 6/2007 | Schwieker | 378/193 |

FOREIGN PATENT DOCUMENTS

| | | |
|---|---|---|
| DE | 6949023 | 5/1971 |
| DE | 6949024 | 5/1971 |
| WO | 2005087105 | 9/2005 |

OTHER PUBLICATIONS

Related non-published U.S. Appl. No. 12/371,492, filed Feb. 13, 2009 and assigned to Leica Microsystems (Schweiz) AG.
Related non-published U.S. Appl. No. 12/371,518, filed Feb. 13, 2009 and assigned to Leica Microsystems (Schweiz) AG.
Related non-published U.S. Appl. No. 12/371,440, filed Feb. 13, 2009 and assigned to Leica Microsystems (Schweiz) AG.

\* cited by examiner

*Primary Examiner* — Ramon Ramirez
*Assistant Examiner* — Todd M Epps
(74) *Attorney, Agent, or Firm* — Schlee IP International, P.C.; Alexander R. Schlee

(57) ABSTRACT

A suspension system for a ceiling mount of a medical device is suggested, comprising an attachment device provided at a ceiling and a console arranged between the attachment device and the ceiling mount for movement of the ceiling mount parallel to the ceiling. Said console comprises a support plate connected to the attachment device and a carriage that is movable with respect to the support plate and is connected to the ceiling mount. This allows movement of the medical device to the greatest extent possible to all positions in the surgical area without colliding with alternately usable operating lights.

15 Claims, 3 Drawing Sheets

SUSPENSION SYSTEM FOR A CEILING MOUNT OF A SURGICAL MICROSCOPE

CROSS-REFERENCE TO RELATED APPLICATION

This application claims the priority of the German patent application DE 102008011311.5 having a filing date of Feb. 27, 2008, the entire content of which is herewith incorporated by reference.

BACKGROUND OF THE INVENTION

The present invention relates to a suspension system for a ceiling mount of a surgical microscope.

In operating rooms for neurosurgery or for ear, nose and throat (ENT) surgery, tomographs are increasingly being used alongside the usual surgical microscopes and illumination and navigation devices. These magnetic resonance imaging (MRI) scanners are integrated directly into the operating room and thus permit an investigation, shortly before the surgical intervention, of the site to be operated on. Because the MRI is integrated into the operating room, the latter is configured as a Faraday cage, and the larger masses of metal present in the operating room have an influence on the image quality of the MRI. It is therefore necessary to adjust the MRI as a function of the metal masses. Subsequent changes in the location of larger metal masses require a readjustment of the MRI.

A further difficulty is the fact that there exists around the MRI a so-called 50-gauss zone in which no metal objects whatsoever must be present. Otherwise these metal objects would be excited to vibrate, and a risk of damage exists. For these safety reasons, no movable stands or components whatsoever are permitted in such operating rooms. All devices attached to stands, such as a surgical microscope, illumination elements, navigation devices, and anesthesia devices, are therefore attached in stationary fashion on the ceiling of the operating room. This is the only way to effectively prevent these units from inadvertently being brought into the 50-gauss zone around the MRI, and thus creating a risk of damage.

A further problem now arises from the fact that because the ceiling mounts are arranged in stationary fashion, only one settable working position is possible. Because of the limited extension range of the individual ceiling mounts, only very restricted optimization of the ceiling-mount arrangement for the microscope and lights in the room may exist, in terms of the surgeon's various positions with respect to the patient. There exists no position for the ceiling mount of the surgical microscope, and for the ceiling mounts of the operating lights, in which every type of operation in the field of neurosurgery or ENT surgery is possible.

In other operating rooms, rail systems on which the surgical microscope or an item of medical equipment is displaceably suspended have already been attached to the ceiling. Rail systems of this kind are known from the documents DE 6949023 U and DE 6949024 U. A disadvantage here is that such rail systems are, in principle, open systems that are not completely sterile. This is not possible in a neurosurgical operating room.

Also known, from WO 2005 087105 A2 and U.S. Pat. No. 4,747,119 A, are rail systems attached to the ceiling that comprise a carrier plate displaceable along the rail system. The mount of a medical device is arranged on the carrier plate. Here again, it is disadvantageous that the rail systems are of open configuration and thus do not represent completely sterile systems. This is not possible in a neurosurgical operating room.

As indicated above, flexible and shiftable floor stands for the surgical microscope must be excluded from this type of operating room with MRI.

SUMMARY OF THE INVENTION

It is therefore an object of the invention to create, in the context of a ceiling mount, the capability for occupying, to the greatest extent possible, all positions in the surgical area without thereby bringing about a collision with the alternately usable operating lights.

It is also necessary to ensure in this context that the very heavy microscope mount (approx. 350 kg) continues to be suspended in vibration-free fashion. A further aspect of the invention may be seen in the fact that no modifications whatsoever are made to the known combinations of the surgical microscope and its ceiling mount.

This object is achieved, according to the present invention, by a suspension system for a ceiling mount of a medical device, comprising an attachment device provided at a ceiling and a console arranged between the attachment device and the ceiling mount for movement of the ceiling mount parallel to the ceiling. Said console comprises a support plate connected to the attachment device and a carriage that is movable with respect to the support plate and is connected to the ceiling mount. This allows movement of the medical device, preferably a surgical microscope, to the greatest extent possible to all positions in the surgical area without colliding with alternately usable operating lights.

The invention is notable for the fact that the console comprises a support plate connected to the attachment device. The support plate in turn is arranged in stationary fashion, and represents the guidance element of a movably configured carriage. The carriage in turn carries the ceiling mount. In a further embodiment of the invention, the support plate has larger dimensions than the carriage, and determines the amount of movement.

In a further embodiment of the invention, the support plate is divided into an upper and a lower plate, the two plates being arranged parallel to one another and being fixedly interconnected via at least two flanges. The result of this is that a cavity that can receive further components is produced between the two plates. In a further embodiment of the invention, provision is thus made for the flanges to be configured, together with the upper and the lower plate, in the manner of a double-T support, thus forming lateral openings for reception of the carriage.

In a further embodiment of the invention, a respective shaped part is arranged at the two lateral ends of the lower plate, parallel to the flanges. A pan is thus formed between the upper and the lower plate. First guidance elements for the carriage are arranged in this pan.

In a further embodiment of the invention, the carriage has a rectangular profile that completely encloses the lower plate.

In a development of the invention, provision is made that the rectangular profile of the carriage engages into the pan between the upper and the lower plate. Associated with the rectangular profile of the carriage are second guidance elements that correspond to the first guidance elements on the lower plate. The carriage is embodied movably along these guidance elements.

In an advantageous development of the invention, the guidance elements can be embodied, for example, as part of a ball, roller, or crossed-roller bearing.

In a development of the invention, the support plate or the lower support plate forms, with the carriage, a sealed system. What is thereby achieved is that despite its embodiment as a mechanical system, no contamination (such as abraded material, oil, or grease) can emerge. This is absolutely necessary especially for mounts in operating rooms. Because the guidance elements are configured and arranged in a pan, contaminants of this kind collect in the pan and are cleaned out during maintenance.

In a development of the invention, provision is made that a hollow ceiling passthrough having at least three support bolts is provided between the ceiling and the support plate.

The hollow ceiling passthrough can be individually configured so that different hollow-ceiling spacings can be compensated for.

In a development of the invention, the console comprises at least three supporting columns between which stiffening flanges are arranged. The stiffening flanges result in excellent mechanical stability and connecting rigidity upon placement of the ceiling mount.

In a development of the invention, provision is made that the carriage is motor-driven in order to enable, despite the heavy weight, simple and reliable positioning of the mount over the desired location.

In a development of the invention, provision is made for this purpose that the motorized drive system comprises a spindle that engages into a spindle nut attached to the carriage. The spindle is equipped with a drive motor. For reliable operation of the motorized drive system, triggering tabs that correspond to electrical limit switches for the drive system are arranged on the spindle nut.

In a development of the invention, a mechanical end stop having a rubber buffer is additionally provided, so that reliable stoppage of the drive system is ensured even in the event of electrical or electronic malfunctions.

In a development of the invention, a skirt is provided on the plate, which skirt serves to separate the circulation of a laminar flow from the ambient air. The laminar flow is a vertically directed low-turbulence air flow that is generated in the region of the surgical site. An improvement in asepsis, especially in the region of the surgical site, is achieved with the laminar flow. It is also therefore evident that despite the use of surgical microscopes in this region, the low-turbulence air flow must continue to be maintained. The result of a skirt is that circulation continues to be ensured, and that the air flow is not influenced by the ambient air.

BRIEF DESCRIPTION OF THE DRAWINGS

In the drawings, which schematically depict an exemplifying embodiment of the present invention.

DETAILED DESCRIPTION OF THE DRAWINGS

Figure 1:
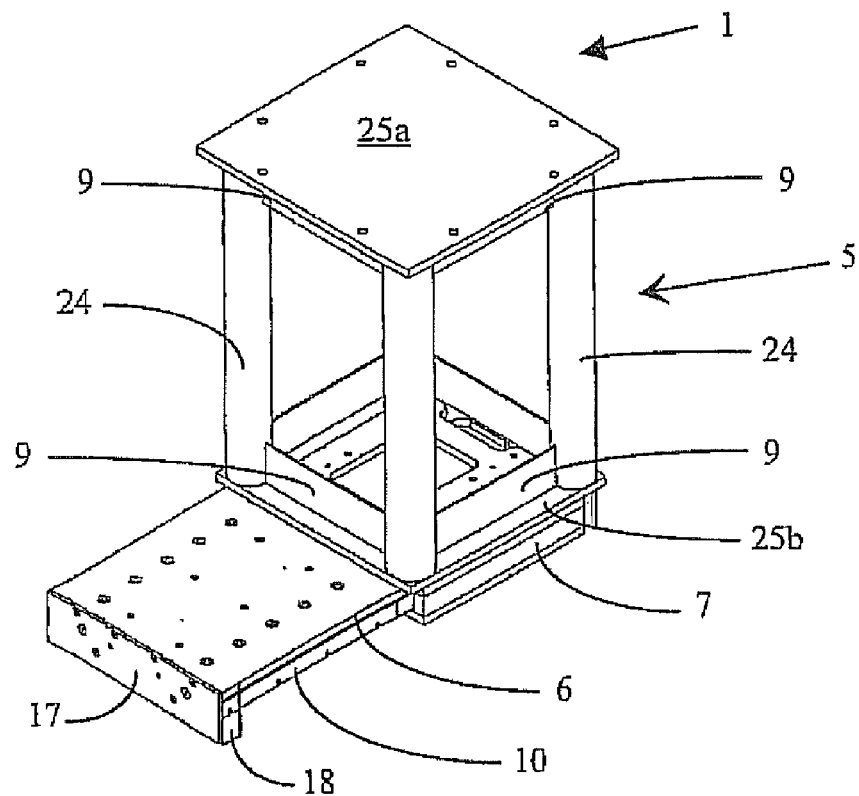
FIG. 1 is a first view of the suspension system.

FIG. 1 is a plan view of suspension system 1. Suspension system 1 contains a console 5 that comprises an upper console plate 25a and a lower console plate 25b. The two console plates 25a, 25b are interconnected via supporting columns 24. Stiffening flanges 9 are arranged between supporting columns 24. Lower console plate 25b carries a support plate 6 that is equipped with a first guidance element 10 for a carriage 7 that is movable along the guidance element. Support plate 6 comprises a rubber buffer 18 and a mechanical end stop 17 as movement limiters for carriage 7.

Figure 2:
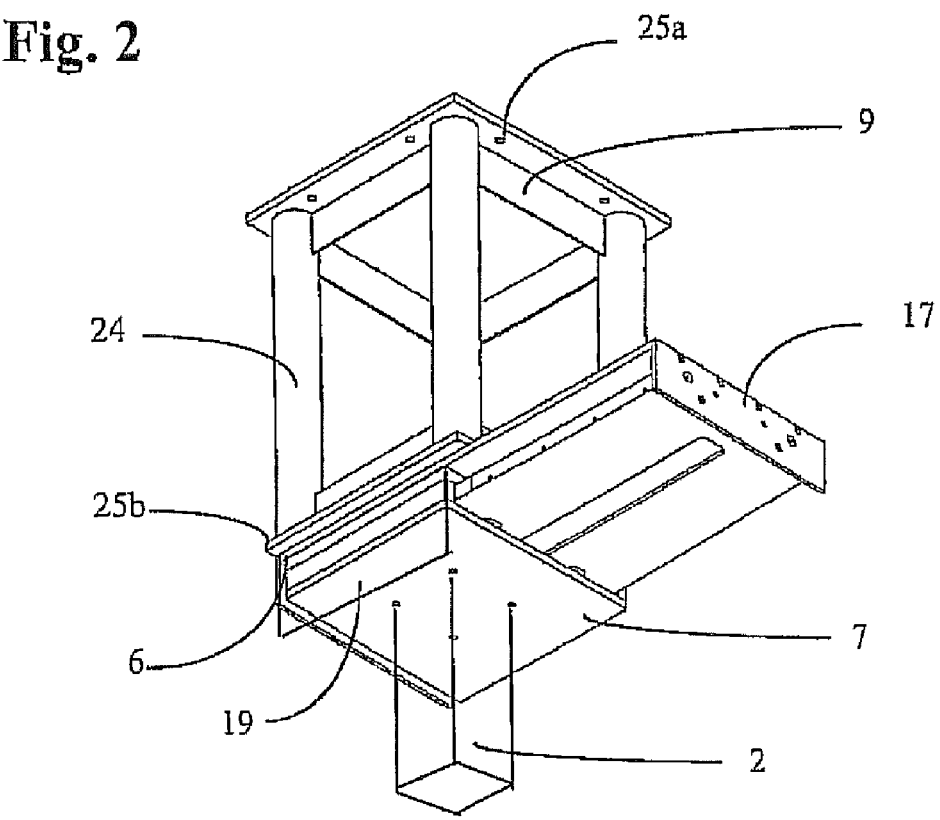
FIG. 2 is a second view of the suspension system with a mount.

FIG. 2 is a second view of the suspension system with mount 2 that is attached to carriage 7. A skirt 19, for separating the circulation of a laminar flow from the ambient air, is also arranged on carriage 7.

Figure 3:
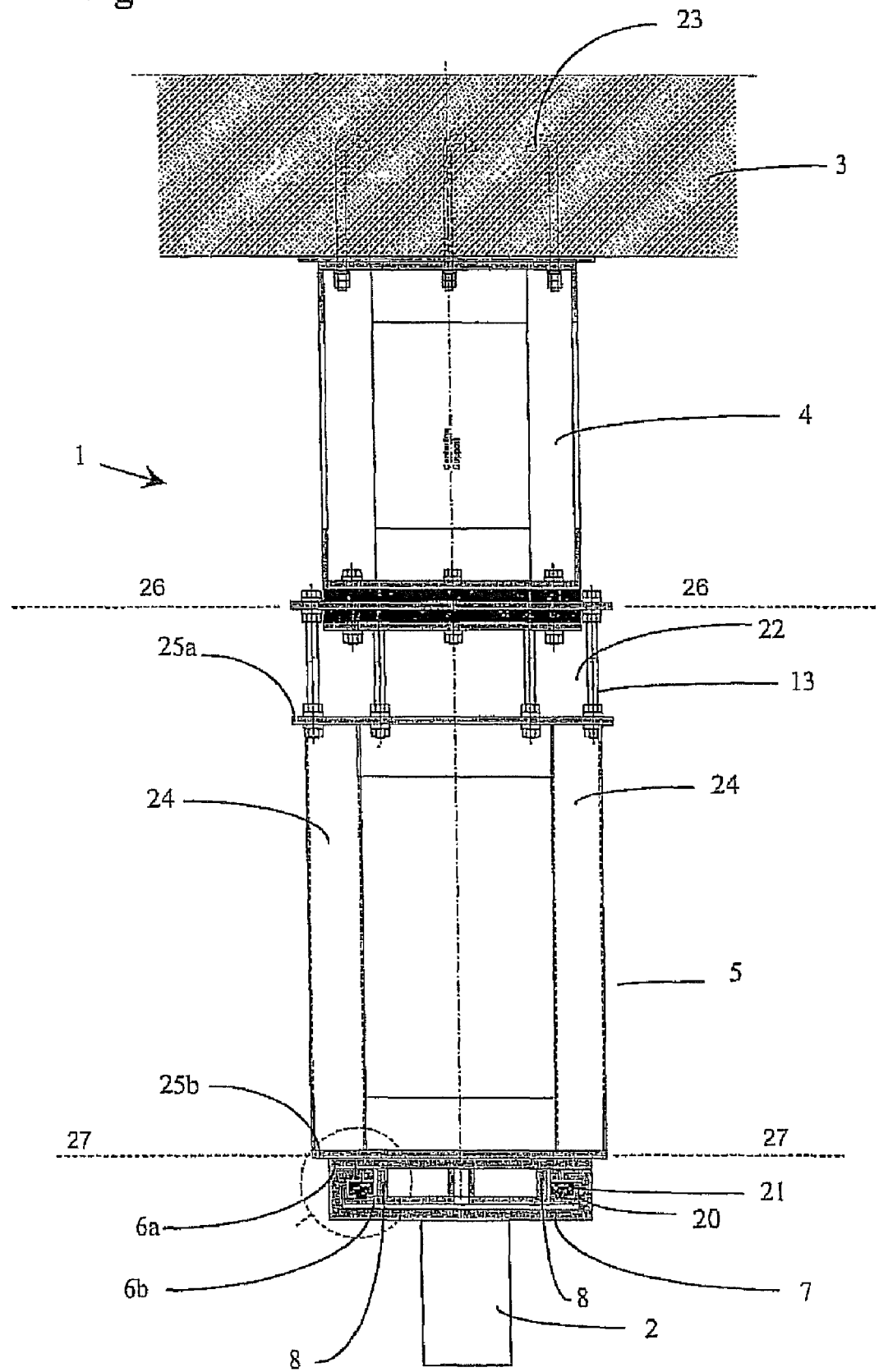
FIG. 3 is a sectioned depiction of the suspension system with a mount.

FIG. 3 is a sectioned depiction of suspension system 1 with an attachment device 4 on ceiling 3. Attachment device 4 comprises for this purpose concrete anchors 23 that are embedded into concrete in ceiling 3. Attachment device 4 carries a hollow ceiling passthrough 22 having support bolts 13. Console 5 is attached to hollow ceiling passthrough 22 with upper console plate 25a. Console plate 25a carries supporting columns 24 and lower console plate 25b. Attached to lower console plate 25b is an upper plate 6a that is connected via two flanges 8 to a lower plate 6b. Attached at each of the two ends of lower plate 6b is a shaped part 20 with which a pan 21 is formed between upper plate 6a and lower plate 6b. A first guidance element 10 is arranged in pan 21 on lower plate 6b.

Provided opposite that element is a second guidance element 12 constituting part of a carriage 7; carriage 7 has a rectangular profile and encloses lower plate 6b. First and second guidance elements 10, 12 can be embodied, for example, as ball or roller or crossed-roller bearings, and permit movement of carriage 7 along lower plate 6b. Carriage 7 carries ceiling mount 2.

Figure 4:
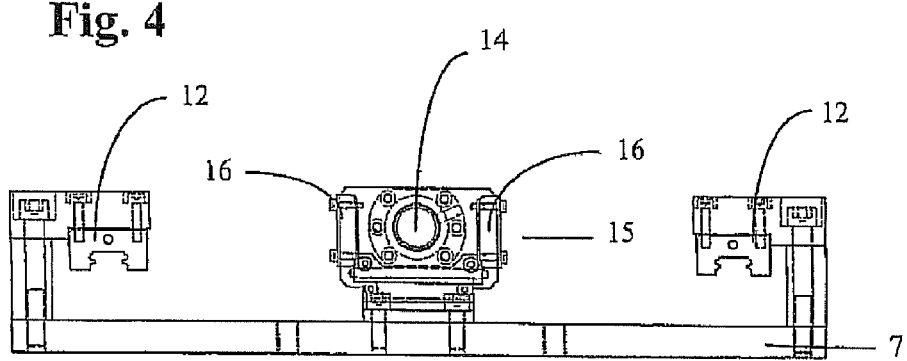
FIG. 4 is a sectioned depiction of the carriage.

FIG. 4 is a sectioned depiction of carriage 7 with second guidance elements 12 and a spindle nut 15. Spindle nut 15 has associated with it a drive spindle 14 that is driven by a motor. Spindle nut 15 further carries two triggering tabs 16 for an optoelectrically operating switching apparatus for the drive motor.

Figure 5:
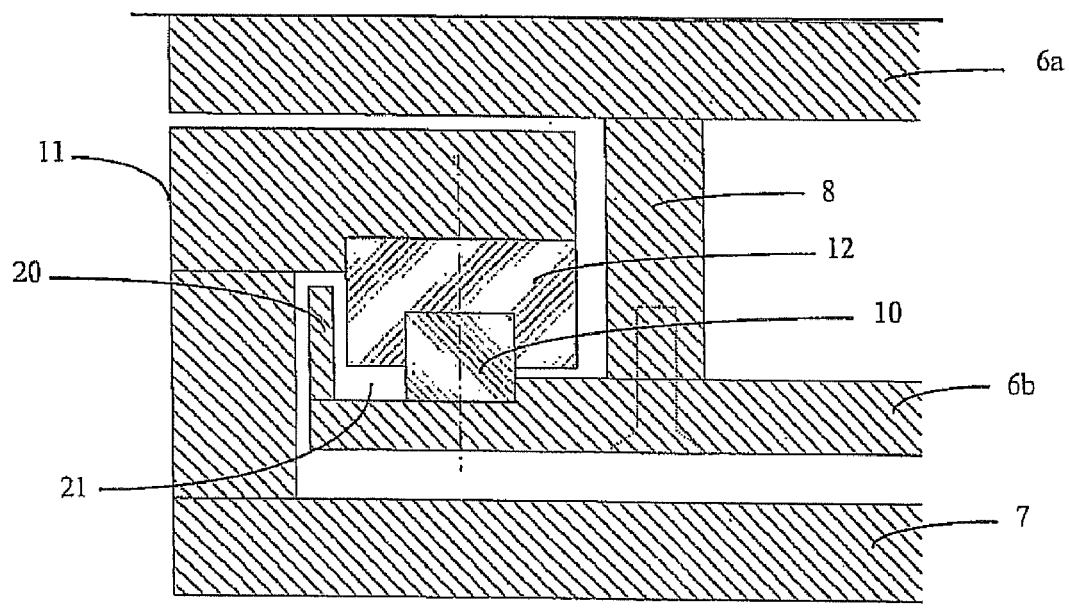
FIG. 5 is a sectioned depiction of guidance elements between the carriage and support plate.

FIG. 5 is a sectioned depiction of the arrangement of carriage 7 on upper and lower plates 6a, 6b. The two plates 6a and 6b are interconnected via a flange 8. Shaped part 20 is provided at the end of lower plate 6b, so that pan 21 is formed between upper plate 6a and lower plate 6b. First guidance element 10 is attached in the pan on lower plate 6b. Carriage 7 engages into this pan with the associated second guidance element 12, and in that context encloses lower plate 6b.

LIST OF COMPONENT PARTS

1 Suspension system
2 Ceiling mount
3 Ceiling
4 Attachment device
5 Console
6 Support plate
6a Upper plate
6b Lower plate
7 Carriage
8 Flange
9 Stiffening flange
10 First guidance elements
11 Rectangular profile
12 Second guidance elements
13 Support bolts
14 Second stiffening flanges
15 Spindle nut
16 Triggering tab
17 Mechanical end stop
18 Rubber buffer 19 Skirt
20 Shaped part
21 Pan
22 Hollow ceiling passthrough
23 Concrete anchor
24 Supporting column
25*a* Upper console plate
25*b* Lower console plate

The invention claimed is:

1. A suspension system for a ceiling mount of a medical device, comprising:
  an attachment device provided at a ceiling; and
  a console arranged between the attachment device and the ceiling mount for movement of the ceiling mount parallel to the ceiling, said console comprising:
  a support plate connected to the attachment device, the support plate comprising an upper plate and a lower plate attached in parallel to each other via at least two connecting elements that are webs, each of which being connected to the upper plate and the lower plate such that a double-T-beam—like connection is formed, providing lateral seats for supporting the carriage; and
  a carriage that is connected to the ceiling mount, said carriage having a rectangular profile that encloses the lower plate, extends into a trough formed between the upper plate and the lower plate and comprises second guidance elements arranged in parallel to one another, wherein the support plate is movable with respect to the carriage.

2. The suspension system for a ceiling mount according to claim 1, wherein the support plate is attached rigidly to the attachment device and extends in a movement direction of the carriage over a length that exceeds a length of that carriage.

3. The suspension system for a ceiling mount according to claim 1, wherein respective shaped parts are provided at the two lateral ends of the lower plate and extend parallel to the respective webs to form respective troughs.

4. The suspension system for a ceiling mount according to claim 1, wherein the lower plate carries first guidance elements at both lateral sides of the lower plate on that side of the plate facing the ceiling.

5. The suspension system for a ceiling mount according to claim 4, wherein the first and second guidance elements are part of one of the group consisting of a ball bearing, a roller bearing and a crossed roller bearing; and the carriage is arranged movably by means of said bearing on the lower support plate.

6. The suspension system for a ceiling mount according to claim 4, wherein the first and second guidance elements are part of one of the group consisting of a ball bearing, a roller bearing and a crossed roller bearing, and the carriage is arranged movably by said bearing on the lower support plate.

7. The suspension system for a ceiling mount according to claim 1, wherein the support plate together with the carriage forms a sealed system.

8. The suspension system for a ceiling mount according to claim 1, wherein a hollow ceiling passthrough having at least three support bolts is provided between the ceiling and the support plate.

9. The suspension system for a ceiling mount according to claim 1, wherein the console comprises at least three supporting columns and stiffening webs are arranged between the supporting columns.

10. The suspension system for a ceiling mount according to claim 1, comprising a motorized drive system for driving the carriage.

11. The suspension system for a ceiling mount according to claim 10, wherein the drive system comprises a powered drive spindle interacting with a spindle nut that is attached to the carriage.

12. The suspension system for a ceiling mount according to claim 11, wherein triggering tabs of an electrical limit switch are arranged at the spindle nut.

13. The suspension system for a ceiling mount according to claim 1, wherein the carriage abuts in an end position against a mechanical end stop having a rubber buffer.

14. The suspension system for a ceiling mount according to claim 1, wherein the carriage is provided with a skirt for separating a circulation of a laminar flow from ambient air.

15. The suspension system for a ceiling mount according to claim 1, wherein the medical device is a surgical microscope.

* * * * *